United States Patent [19]

Doi et al.

[11] Patent Number: 4,783,787
[45] Date of Patent: Nov. 8, 1988

[54] LASER BEAM GENERATING DEVICE WITH MULTIPLE POWER LEVELS

[75] Inventors: Yuzuru Doi; Hironobu Nagashima, both of Tokyo, Japan

[73] Assignee: Asahi Kogaku Kogyo Kabushiki Kaisha, Tokyo, Japan

[21] Appl. No.: 871,038

[22] Filed: Jun. 5, 1986

[30] Foreign Application Priority Data

Jun. 12, 1985 [JP] Japan .................................. 60-128966

[51] Int. Cl.⁴ ............................................. H01S 3/13
[52] U.S. Cl. ......................................... 372/31; 372/33; 372/9; 372/26; 372/108; 372/19
[58] Field of Search .................. 372/31, 29, 9, 14, 15, 372/26, 28, 108, 19

[56] References Cited

U.S. PATENT DOCUMENTS

| | | | |
|---|---|---|---|
| 3,286,183 | 11/1966 | Koster et al. | 372/14 |
| 3,561,869 | 2/1971 | Cason, III et al. | 372/14 |
| 3,609,588 | 9/1971 | McKnight | 372/15 |
| 3,626,322 | 12/1971 | Tobias et al. | 372/99 |
| 4,435,808 | 3/1984 | Javan | 372/26 |
| 4,514,849 | 4/1985 | Witte et al. | 372/26 |
| 4,566,453 | 1/1986 | Kumano et al. | 372/87 |

Primary Examiner—Leon Scott, Jr.
Attorney, Agent, or Firm—Sughrue, Mion, Zinn, Macpeak & Seas

[57] ABSTRACT

A laser beam generating device that can vary its output by mechanical means. The laser output can selectively be chopped by selectively moving a chopping wheel into the path of the laser beam, whereby full power is obtained without the chopper and reduced power is obtained with the chopper.

13 Claims, 2 Drawing Sheets

LASER BEAM GENERATING DEVICE WITH MULTIPLE POWER LEVELS

BACKGROUND OF THE INVENTION

1. Field of the Invention

This invention relates to means for attenuating the power of a laser beam in a laser-operated medical treatment device which is used, for instance, as a laser knife.

2. Background Art

A $CO_2$ laser beam and an Nd-YAG laser beam are generally employed for a laser-operated medical treatment device which utilizes the thermal energy of a laser beam. In the case where an endoscope is used, an Nd-YAG laser is extensively employed because its beam is effectively transmitted through the flexible optical fiber transmitting the laser output. A contact type medical treatment has been put into practice in which a transparent sapphire member is attached to the end of the optical fiber receiving the beam from an Nd-YAG laser, and the diseased part is cut or congealed with the end of the sapphire member held in contact therewith.

In the contact type medical treatment, the transparent sapphire member is brought into direct contact with the diseased part as was described above, and therefore reflection and scattering of the laser beam at the diseased part are suppressed. Accordingly, in the contact type medical treatment, medical treatment can be carried out with low laser power and the effect is greater than with the same power in a non-contact type medical treatment. In the case of congealing the diseased part, the non-contact type medical treatment requires a laser power of more than 30 W, while in the contact type medical treatment the same effect can be obtained with a laser power which is about one-third ($\frac{1}{3}$) of this value.

On the other hand, in stopping bleeding, the Nd-YAG laser beam should have a high power of the order of 100 W. Accordingly, in order to use an Nd-YAG laser beam generator as a general-purpose laser beam generator, the Nd-YAG laser beam generator should be able to generate a laser beam in a range of from a low output of several watts to a high output of 100 W or higher.

However, it is impossible for a conventional 100 W Nd-YAG laser beam generator to stably provide a low output of the order to 10 W because, in the laser beam generator, the threshold value for population inversion for starting laser beam generation corresponds to an output of about 10 W. That is, if current control is carried out so that the intensity of the exciting lamp is changed for a low output, then the laser beam generated is considerably unstable. Therefore, heretofore, the above-described contact type medical treatment was required to use a special low-output Nd-YAG laser beam generator.

SUMMARY OF THE INVENTION

Accordingly, an object of this invention is to eliminate the above-described difficulties accompanying a conventional laser beam generating device.

More specifically, an object of the invention is to provide a general purpose laser beam generating device which can provide a laser beam over a range extending from a low output power to a high output power.

A laser beam generating device of the invention has been developed by using the approach that a high power laser beam is provided by a laser beam generator. For high power operation, the laser beam is used as it is. For low power operation, part of the laser beam is periodically intercepted by a light intercepting unit. Therefore, in the invention, a light intercepting unit for mechanically intercepting the laser beam at a predetermined rate is caused to go in and out of the optical path of the laser beam.

DETAILED DESCRIPTION OF THE PREFERRED EMBODIMENTS

This invention will be described reference to its preferred embodiments.

Figure 1:
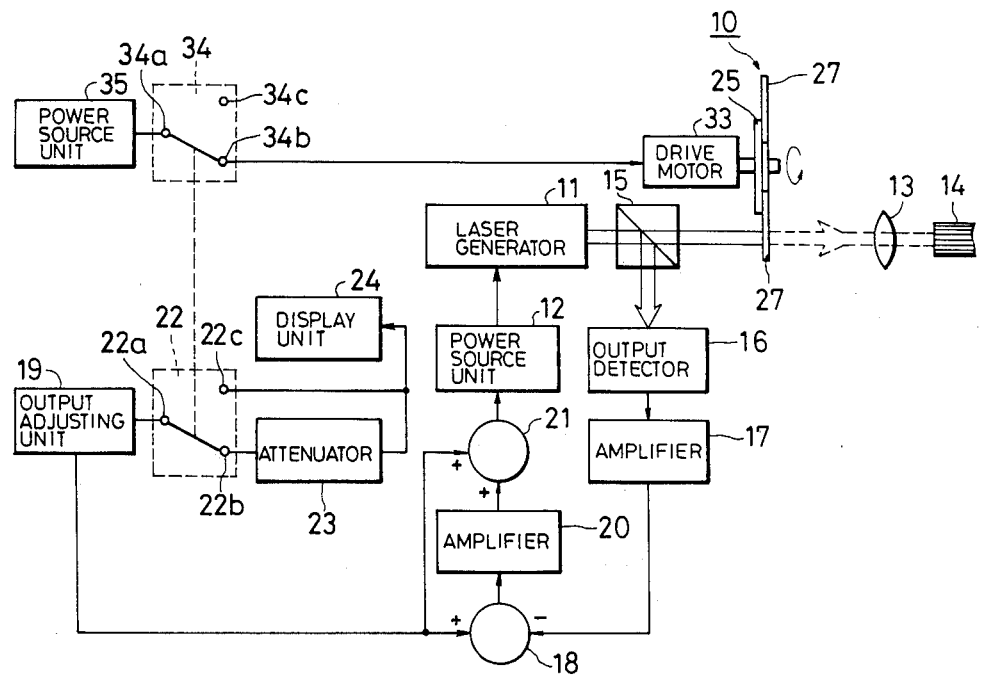
FIG. 1 is a block diagram showing a first example of a laser beam generating device according to this invention.

FIG. 1 is a block diagram showing a first example of a laser beam generating device according to the invention. FIG. 2 shows one example of a light intercepting unit 10 in FIG. 1.

In the laser beam generating device, a laser generator 11 is energized by the output power of a power source unit 12, to thereby generate a laser beam. The laser beam thus generated is applied through a condenser lens system 13 to the incident end face of a laser fiber 14, which is used, for instance, for laser-based medical treatment.

A beam splitter 15 is arranged in the optical path between the laser generator 11 and the condenser lens system 13, to split the laser beam into two parts. One of the two parts is applied to the condenser lens system 13 as was described above, and the other part is applied to an output detector 16. The output of the detector 16, after being amplified by an amplifier 17, is applied to an arithmetic circuit 18. The output of an output adjusting unit 19 is also applied to the arithmetic circuit 18. The arithmetic circuit 18 compares the output of the output detector 16 with the output of the output adjusting unit 19, and calculate the difference between them. The difference of the comparison is applied through an amplifier 20 to a addition circuit 21, to which the output of the output adjusting unit 19 is applied. The output of the addition unit 21 controls the power source unit 12. That is, the addition circuit 21 controls the power source unit 12 according to the sum between the output of the arithmetic circuit 18 and the output of the output adjusting unit 19. That is, with the aid of the above-described feedback system, the laser beam generator 11 is driven by the power source unit 12 so that the intensity of the generated laser beam becomes an output value set by the output adjusting unit 19.

On the other hand, as a high and low change-over switch 22 is operated, an output of the output adjusting unit 19 is applied through an attenuator 23 to a display unit 24, or applied directly to the display unit 24.

The light intercepting unit 10 is so provided that it can go in and out of the laser beam between the laser beam generator 11 and the condenser lens system 13.

Figure 2A:
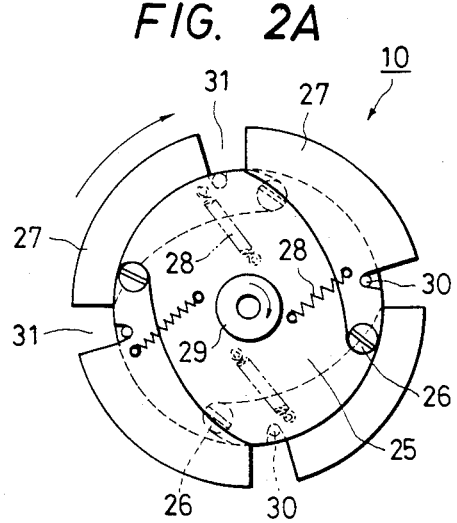
FIGS. 2A and 2B are front view of one example of a light intercepting unit in the device of the invention, showing the two different states of the unit.
Figure 2B:
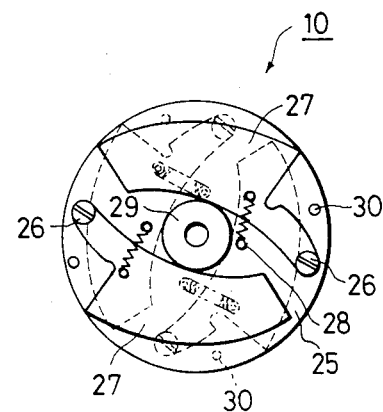

More specifically, the light intercepting unit 10, as shown in FIGS. 2A and 2B, comprises a rotary disc 25 and four light intercepting plates 27 arranged on the periphery of the rotary disc 25 at angular intervals of 90°. Two of the light intercepting plates 27 are disposed on the front side of the rotary disc and the other two light intercepting plates 27 are disposed on the back side. Each of the light intercepting plates 27 is pivotally mounted on a respective pin 26 embedded in the rotary disc 25 so that the light intercepting plate 27 can swing about the pin 26 outwardly and inwardly of the outer circumference of the rotary disc 25. Ordinarily, the light intercepting plates 27 are held inside the rotary disc 25 by tension springs 28 as shown in FIG. 2B. However, when the speed of the rotary disc 25 reaches a predetermined value, i.e., the centrifugal force applied thereto reaches a certain value, the light intercepting plates 27 are caused to swing outside the outer circumference of the rotary disc 25 as shown in FIG. 2A. As shown clearly in FIG. 2B, a stopper disc 29 regulates the swing-in positions of the light intercepting plates 27, and, as shown in FIG. 2A, stopper pins regulate the swing-out positions of the plates 27. When the light intercepting plates 27 are swung to the swing-out positions, they project into the laser beam path. Under this condition, a rotational gap 31 is formed between adjacent light interception plates 27 as shown in FIG. 2A. The ratio of the total circumferential length of the gaps 31 to the total circumferential length of the light intercepting plates is preferably about 1:4.

As shown in FIG. 1, the rotary disc 25 is rotated by a drive motor 33 which is connected through an operating switch (or a high and low change-over switch) 34 to a power source unit 35. The operating switch 34 is operated in association with the aforementioned high and low change-over switch 22.

In the laser beam generating device thus constructed, a low output mode can be selected by causing the armatures of the switches 22 and 34 to take the low output positions, i.e., by connecting the contact 22a to the contact 22b in the operating switch 22 and by connecting the contact 34a to the contact 34b in the change-over switch 34. When the switches 22 and 34 are operated in this manner, the drive motor 33 is energized to rotate the rotary disc 25. When the speed of the rotary disc 25 reaches the predetermined value, the light intercepting plates 27 project into the laser beam path as was described above. As a result, a part of the laser beam applied from the laser beam generator 11 to the condenser lens system 13 is mechanically intercepted so that the intensity of the laser beam incident on the condenser lens system 13 is decreased.

As was described above, the ratio of the total circumferential length of the gaps 31 to the total circumferential length of the light intercepting plates is 1:4 in the described embodiment. Therefore, the chopping action of the light intercepting plates 27, caused by the rotation of the rotary disc 25, decreases the output of the laser beam generator 11 to one-fifth (1/5) its unattenuated value, and the output thus decreased is applied to the laser fiber 14. For instance, when the output of the laser beam generator 11 is 100 W, the output is decreased to 20 W, and when the output is 10 W, it is decreased to 2 W. The output decreased in this manner is applied to the condenser lens system 13. Even if the rotation of the rotary disc 25 is not uniform, the ratio of the total circumferential length of the gaps 31 to the total circumferential length of the light intercepting plates 27 is constant, and therefore the attenuated laser beam is stably applied to the condenser lens system. The attenuator 23 has an attenuation corresponding to the aforementioned ratio. In the low output mode, the attenuator 23 attenuates the set output of the output adjusting unit 19 to one-fifth (1/5) its unattenuated value, and the output thus attenuated is displayed on the output display unit 24. In other words, a value equivalent to the output value of the laser beam which has been attenuated by the light intercepting unit 10 is displayed on the output display unit 24.

Figure 3:
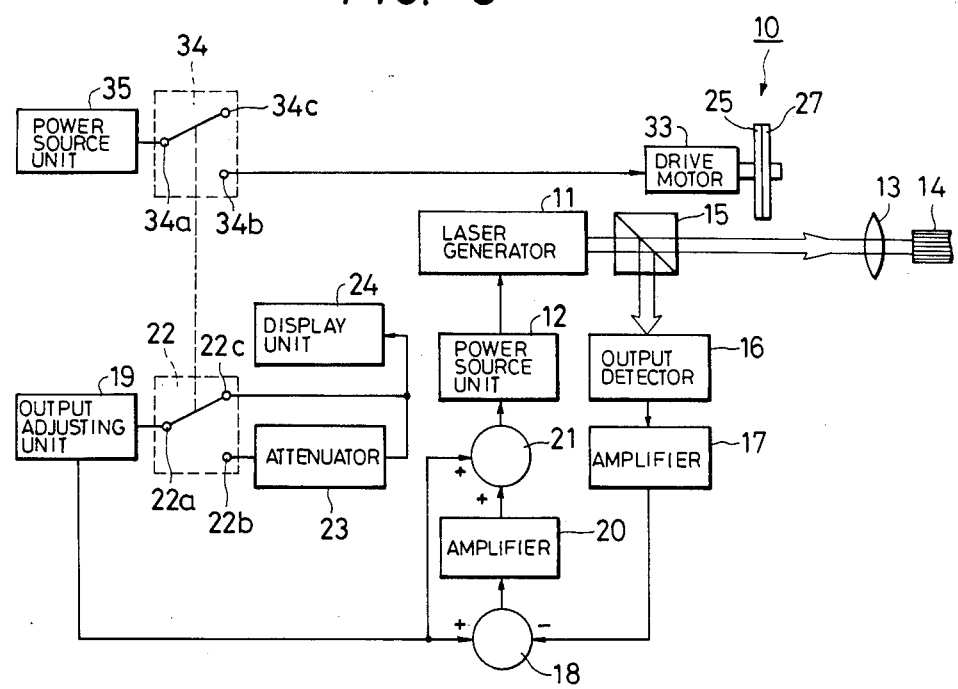
FIG. 3 is a block diagram showing the laser beam generating device of FIG. 1 in which a high output mode is selected.

On the other hand, a high output mode is selected by operating the high and low change-over switch 22 and the operating switch 34 in such a manner that the contact 22a is connected to the contact 22c in the operating switch 22 while the contact 34a is connected to the contact 34c in the change-over switch 34, as shown in FIG. 3. In this case, the drive motor 33 is electrically disconnected from the power source unit 35, and therefore the rotary disc 25 is not rotated. The set output of the output adjusting unit 29 is displayed directly on the output display unit 24. Accordingly, the light intecepting plates 27 of the light intercepting unit 10 are retracted inside the rotary disc 25 by the elastic force of the tension springs 28 as shown in FIG. 2B. Therefore, the laser beam outputted by the laser beam generator 11 is not mechanically attenuated; that is, it is applied directly through the condenser lens system 13 to the laser fiber 14.

Insertion of the light intercepting unit 10 in the laser beam path in front of the beam splitter as described above has the advantage that a conventional monitoring device can be utilized, as it is, for detecting and processing the monitor signal (or laser beam) provided by the beam splitter 15.

Figure 4:
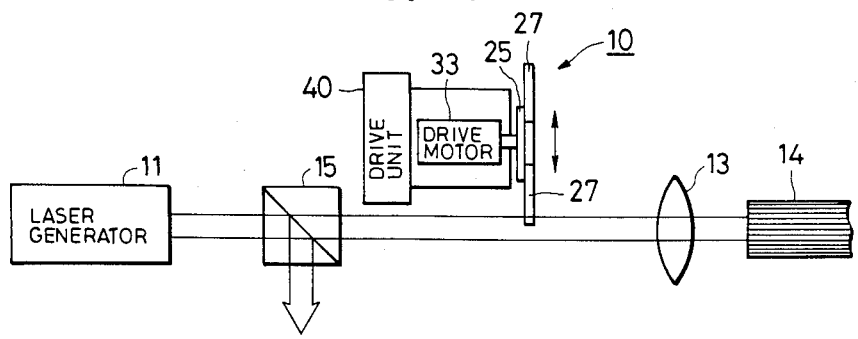
FIG. 4 is a block diagram showing a second example of the laser beam generating device according to the invention.

FIG. 4 shows a second example of the laser beam generating device according to the invention. The second example employs a light intercepting unit 10 in which the light intercepting plates 27 are fixed to the rotary disc 25 as shown in FIG. 2A and do not move outwards. A drive unit 40 causes the entire light intercepting unit 10 to move in the illustrated vertical direction, in and out of the laser beam path, as shown in FIG. 4. The other elements of the second example are the same as those which have been shown in FIGS. 1 and 3. A purality of light intercepting units 10 different in the ratio of the total circumferential length of the gaps 31 to that of the light intercepting plates 27 are provided. The light intercepting units 10 are caused to go in and out of the laser beam path, one at a time, by the respective drive units 40, as a result of which the laser beam is attenuated with different attenuation factors. That is, not only two output modes, namely, the high and low output modes, can be obtained but also additional output modes between the high and low output modes.

As was described above, in the laser beam generating device of the invention, the light intercepting unit is caused to go in and out of the laser beam path to mechanically intercept a part of the laser beam generated. Accordingly, the intensity of the laser beam outputted can be controlled readily, and even in the low output mode the laser beam output is stably maintained. Therefore, if the device of the invention is applied to a laser-operated medical treatment device, then a high laser output can be obtained for a non-contact medical treatment, and a stable low laser output can be provided in the contact medical treatment which is carried out with a transparent sapphire member attached to the fiber emergent end face.

What is claimed is:

1. A laser beam generating device for the selectable delivery of a power laser beam at one of a first and second power level, said laser beam generating device comprising:
   a laser for producing an output laser beam;
   light interrupting means selectively disposed along a path of said output laser beam, said light interrupting means having light interrupting plate means for mechanically interrupting said output laser beam at a predetermined rate; and
   means for selectively operating said light interrupting plate means in one of:
   a first mode of operation wherein said light interrupting plate means does not interrupt said output laser beam so that said laser beam generating means delivers a laser beam at a maximum power level corresponding to an uninterrupted said output laser beam; and
   a second mode of operation wherein said light interrupting plate means periodically interrupts said output laser beam so that said laser beam generating means delivers a laser beam having a power level reduced blow said maximum power level in correspondence with the periodic interruption of said output laser beam.

2. A device as recited in claim 1, further comprising:
   an optical detector;
   a beam splitter disposed along said path for directing a part of said output laser beam to said detector;
   control means responsive to an output of said detector for controlling a power level of said laser.

3. A device as recited in claim 2, wherein said beam splitter is disposed on a portion of said path between said laser and said light interrupting means.

4. A laser beam generating device for the selectable delivery of a power laser beam at one of a first and second power level, said laser beam generating device comprising:
   a laser for producing an output laser beam along a beam path; and
   light interrupting means for mechanically interrupting said output laser beam at a predetermined rate, said light interrupting means being disposed adjacent to said path of said output laser beam and comprising;
   a rotary disc,
   means for rotating said rotary disc at at least first and second speeds,
   light interrupting plate means pivotally mounted on a periphery of said disc and being outwardly openable into said path of said output laser beam,
   biasing means for biasing said light interrupting plate means inwardly on said disc, said biasing means being effective to operate said plate means in at least first and second states,
   wherein, in said first state said plate means does not intercept said output laser beam during operation of said rotary disc at said first speed or below so that said laser beam generating device delivers a maximum power laser beam corresponding to an uninterrupted said output laser beam, and
   wherein, in said second state, said biasing means is operable so that when the speed of rotation of said rotary disc is at least at said second speed, which exceeds a predetermined value, a centrifugal force acts on said light intercepting plate means to overcome said biasing means such that said plate means are outwardly opened to periodically interrupt said output laser beam, so that said laser beam generating device delivers a laser beam having a power level reduced below said maximum power level in correspondence with the periodic interruption of said output laser beam.

5. A device as recited in claim 4, further comprising:
   an optical detector;
   a beam splitter disposed along said path for directing a part of said output laser beam to said detector;
   control means responsive to an output of said detector for controlling a power level of said laser.

6. A device as recited in claim 5, wherein said beam splitter is disposed on a portion of said path between said laser and said light interrupting means.

7. A device as recited in claim 6, further comprising output adjusting means for setting a desired output level of said laser, said output adjusting means outputting an output level signal, wherein said control means receives and is responsive to said output level signal.

8. A device as recited in claim 7, further comprising:
   output display means for producing a visual display identifying the setting of said output level of said laser, said output display means receiving said output level signal from said output adjusting means;
   attenuator means for attenuating said output level signal being received by said output display means, during times when said means for rotating is being operated at said second speed; and
   means for selectively inserting said attenuator means between an input to said output display means and said output of said output adjusting means, during times when said means for rotating is being operated at said second speed.

9. A device as recited in claim 8, further comprising:
   a selectable operating switch for controlling the operation of said means for rotating in one of said first and second speeds; and
   a change-over switch for controlling a selective insertion function of said means for selectively inserting, said change-over switch being responsive to a selection of said operating switch.

10. A laser beam generating device for the selectable delivery of a power laser beam at any one of a plurality of power levels, said laser beam generating device comprising:
    a laser producing an output laser beam;
    rotary disc means having a periphery with periodically spaced projections;
    means for rotating said rotary disc means at a predetermined rate; and
    means for selectively moving said rotary disc means between first and second positions wherein:
    in said first position, said spaced projections do not interrupt said output laser beam so that said laser beam generating device delivers a laser beam at a maximum power level corresponding to an uninterrupted output laser beam; and
    in said second position, said spaced projections do interrupt said output laser at a periodic predetermined rate so that said laser beam generating device delivers a reduced power laser beam having a power level reduced below said maximum power level in correspondence with the periodic interruption of said output laser beam.

11. A device as recited in claim 10, further comprising:
an optical detector;
a beam splitter disposed along a path of said output laser beam for directing a part of said output laser beam to said detector;
control means responsive to an output of said detector for controlling a power level of said laser.

12. A device as recited in claim 11, wherein said beam splitter is disposed on a portion of said path between said laser and said rotary disc means.

13. A device as recited in claim 11, comprising a plurality of rotary disc means having periodically spaced projections of different periods and wherein said means for selectively moving moves a selected one of said rotary disc means between said first and second positions.

* * * * *